(12) United States Patent
Plant et al.

(10) Patent No.: US 7,909,367 B2
(45) Date of Patent: Mar. 22, 2011

(54) CAPILLARY INTERCONNECTION FITTING AND METHOD OF HOLDING CAPILLARY TUBING

(75) Inventors: Kenneth R. Plant, Leominster, MA (US); Sylvain Cormier, Ashland, MA (US); Geoff C. Gerhardt, Millbury, MA (US)

(73) Assignee: Waters Technologies Corporation, Milford, MA (US)

( * ) Notice: Subject to any disclaimer, the term of this patent is extended or adjusted under 35 U.S.C. 154(b) by 509 days.

(21) Appl. No.: 11/072,485

(22) Filed: Mar. 4, 2005

(65) Prior Publication Data

US 2006/0113794 A1    Jun. 1, 2006

Related U.S. Application Data

(63) Continuation of application No. PCT/US03/28128, filed on Sep. 9, 2003.

(60) Provisional application No. 60/410,346, filed on Sep. 12, 2002.

(51) Int. Cl.
*F16L 33/00* (2006.01)
(52) U.S. Cl. ........................................ 285/249; 285/342
(58) Field of Classification Search .................. 285/342, 285/334.3, 332.2, 249; 210/198.2
See application file for complete search history.

(56) References Cited

U.S. PATENT DOCUMENTS

| | | | |
|---|---|---|---|
| 4,451,364 A | 5/1984 | Higgins et al. | |
| RE31,974 E | 8/1985 | Brownlee | |
| 4,586,733 A | 5/1986 | Anderson, Jr. et al. | |
| 4,787,656 A | 11/1988 | Ryder et al. | |
| 4,861,473 A | 8/1989 | Shackelford et al. | |
| 5,234,235 A | 8/1993 | Worden et al. | |
| 5,525,303 A | 6/1996 | Ford et al. | |
| 5,582,723 A | 12/1996 | Boone et al. | |
| 5,938,919 A | 8/1999 | Najafabadi et al. | |
| 6,095,572 A * | 8/2000 | Ford et al. | 210/198.2 |
| 6,102,449 A | 8/2000 | Welsh | |
| 6,162,362 A | 12/2000 | Ma et al. | |
| 6,190,616 B1 | 2/2001 | Jovanovich et al. | |
| 6,319,476 B1 | 11/2001 | Victor et al. | |
| 6,494,500 B1 | 12/2002 | Todosiev et al. | |
| 2001/0007641 A1 | 7/2001 | Jovanovich et al. | |

* cited by examiner

*Primary Examiner* — Aaron Dunwoody
(74) *Attorney, Agent, or Firm* — Anthony J. Janiuk; Sigun Huang

(57) ABSTRACT

The present invention is a capillary interconnection fitting and method of clamping a capillary in the fitting that separates a forward ferrule that holds the capillary from a secondary clamping device. The fitting comprises a sealing ferrule, a compression screw and a clamping device. The ferrule is fitted in a compression screw that mates to a fluidic component. The clamping device is decoupled from the ferrule and coupled to the compression screw.

6 Claims, 5 Drawing Sheets

CAPILLARY INTERCONNECTION FITTING AND METHOD OF HOLDING CAPILLARY TUBING

CROSS REFERENCE TO RELATED APPLICATIONS

This application claims benefit of and is a continuation of International Application No. PCT/US03/28128, filed Sep. 9, 2003 and designating the United States, which claims benefit of and priority to U.S. Provisional Application No. 60/410,346, filed Sep. 12, 2002. The entire contents of these applications are incorporated herein by reference

FIELD OF THE INVENTION

The invention relates to interconnection systems useful in high pressure fluidic systems such as high performance liquid chromatography systems.

BACKGROUND OF THE INVENTION

In conventional-scale liquid chromatography, the mobile phase liquid is usually conveyed between components of the chromatography system in tubing constructed from stainless steel, poly-ether-ether-ketone (PEEK™), or fluoridated hydrocarbon polymers such as those marketed using trademarks like Teflon® (Dupont). Conventional chromatography is typically practiced with analytical columns having a typical internal diameter in the range of 3.9 to 4.6 millimeters. A typical external diameter for interconnection tubing is nominal $1/16^{th}$ inch (approximately 0.062" or 1.57 mm). The internal diameter of the interconnection tubing will generally vary with the type of application, but diameters ranging from 0.005" to 0.040" (0.127 to 1.02 mm) are common.

In recent years, interest has grown in the practice of liquid chromatography at capillary size scales. Capillary tubing is typically formed from fused silica (a type of glass) and will have an outside diameter in the range of 360 microns and an inside diameter in the range of 25 to 100 microns. The internal diameter of a capillary scale analytical column may range from 800 microns to 50 microns or less. For a column of 75 micron internal diameter, the volume of an eluting zone or band will typically be less than 100 nanoliter. In order to effect connections of a system incorporating a 75 micron diameter column, the connecting tubing will typically be chosen to have an internal diameter of 25 microns or less. As capillary size has decreased, fluid pressure in fluid handling devices has generally increased.

These dynamics have put tremendous stress on capillary fittings. One difficulty at high pressures has been simply retaining a capillary in a fitting.

Typically, a capillary tube is held in a fitting by a ferrule and compression screw that presses on the ferrule to provide the fluidic seal between the capillary and whatever it is joined with. No additional mechanisms for holding the capillary tube other than with the grip provided by the sealing ferrule in such a fitting have been required for high pressures (5,000 to 30,000 psi). However, as the pressure increases in fluid handling systems, a more secure gripping of the capillary in a fitting has become necessary. The ferrule/compression screw design provides insufficient retention of a capillary at ultra high pressure (30,000 to 100,000 psi). The insufficient clamping force of the ferrule/compression screw design results in the capillary being ejected from the fitting as fluid pressure is increased.

SUMMARY OF THE INVENTION

The present invention provides a method and mechanism for reliably securing tubing in a reusable fitting. The fitting is suitable for connecting the tubing to or disconnecting the tubing from other fluid components in a system operating at ultra high pressures. By providing a secondary clamping force in addition to the clamping force of a primary ferrule, the invention is able to hold a capillary in position at very high pressures. The invention permits reliable fluidic interconnections at pressures up to 100,000 psi. The preferred fluid handling system for the present invention withstands pressure in the range of 15,000 psi to 100,000 psi and uses fused silica capillaries as tubing. Such a handling system has special utility in ultra high pressure, high performance liquid chromatography systems.

The primary or forward ferrule of the invention is decoupled from a secondary clamping device. By separating the two mechanisms, the present invention can provide quick fluid seals, prevent the capillary tube from being damaged due to creeping forward when being tightened and prevent the capillary tube from ejecting when under pressure. A fitting of the present invention includes a forward ferrule providing a high unit pressure fluidic seal to a capillary tube and a fluidic receptacle The forward ferrule is adapted to easily connect and disconnect to an appropriate female receptacle. The preferred embodiment provides a compression screw to exert sufficient sealing pressure on the forward ferrule. The threaded exterior of the compression screw can easily mate with an oppositely threaded port of a fluidic component incorporating the female receptacle.

The secondary clamping device is in a fixed relationship with the compression screw and forced into engagement with the capillary tube by mechanical means. This device is adapted to provide sufficient frictional force between the capillary and the secondary clamping device to prevent fluid pressure from forcing the capillary tube out of the fitting assembly.

By decoupling the activation of the forward fluidic sealing ferrule by a first device (i.e. the compression screw) from the capillary tube clamping device, the fitting is installed in two stages. First the forward ferrule and compression screw are installed in a female receptacle to house the capillary; the ferrule providing a fluid tight seal with a fluidic component. The secondary clamp is fitted thereafter to provide a clamping force to grip the capillary tube. This clamping force prevents the capillary tube from blowing out of the forward ferrule and the sequence of installation prevents the capillary from creeping forward when the secondary clamp is tightened down. The secondary clamp is constrained from rotating about the capillary tube to protect the capillary from potentially damaging twisting loads.

In one embodiment, a forward fluidic sealing ferrule and compression screw at the end of the capillary tubing provide a high unit pressure fluid seal when installed in an appropriately mated receptacle. The forward ferrule has an axial bore for the capillary and the compression screw has an axial bore for the capillary and a capillary sleeve. An axial passage is provided through a clamping plate for the capillary tube and protective capillary sleeve. Clamping screws are used to join the clamping plate with a clamping collar to hold the protective sleeve with the capillary tube in place. The clamping collar has an axial passage corresponding to that of the clamping plate such that when the parts are joined an axial bore is created to provide a housing for the capillary and sleeve.

A second embodiment provides an external, tapered collapsible collet as the secondary clamping device. The secondary clamping device is activated by a second compression screw having a matching internal taper to the collet. The action of the secondary clamping device is decoupled from the forward ferrule.

The collet has an axial bore that surrounds a protective sleeve and capillary tube and is collapsed around the protective sleeve capturing the capillary tube.

The present invention has the advantage of providing a means for creating reliable fluid interconnections at what is considered ultra-high fluid pressures (30,000 to 100,000 psi) without the danger of capillary tube ejection from its fitting. The device makes possible multiple disconnect and reconnect cycles of the same fitting in systems operating at this pressure level. It also has the advantage of complete disassembly and reassembly without damaging the capillary tube so that the capillary tube and the components of the fitting assembly may be reused.

The present invention permits the assembly of a capillary tube to a fluidic component via the fitting in two stages where the fluid tight ferrule and compression screw are installed first and the secondary clamping device is installed thereafter. It further provides protection for the capillary from twisting and compression loads, which can cause the capillary to break.

BRIEF DESCRIPTION OF THE DRAWINGS

The above noted and other features of the invention will be better understood from the following detailed description, when considered in connection with the accompanying drawings, in which.

DETAILED DESCRIPTION OF THE DRAWINGS

The numerous teachings of the present application will be described with particular reference to the presently preferred embodiment. However, it should be understood that these embodiments provide only a few examples of the advantageous uses of the teachings herein. In general, statements made in the specification of the present application do not necessarily delimit any of the various claimed inventions. It will be obvious to those skilled in the art that various modifications can be made without departing from the spirit and scope of this invention.

Figure 1:
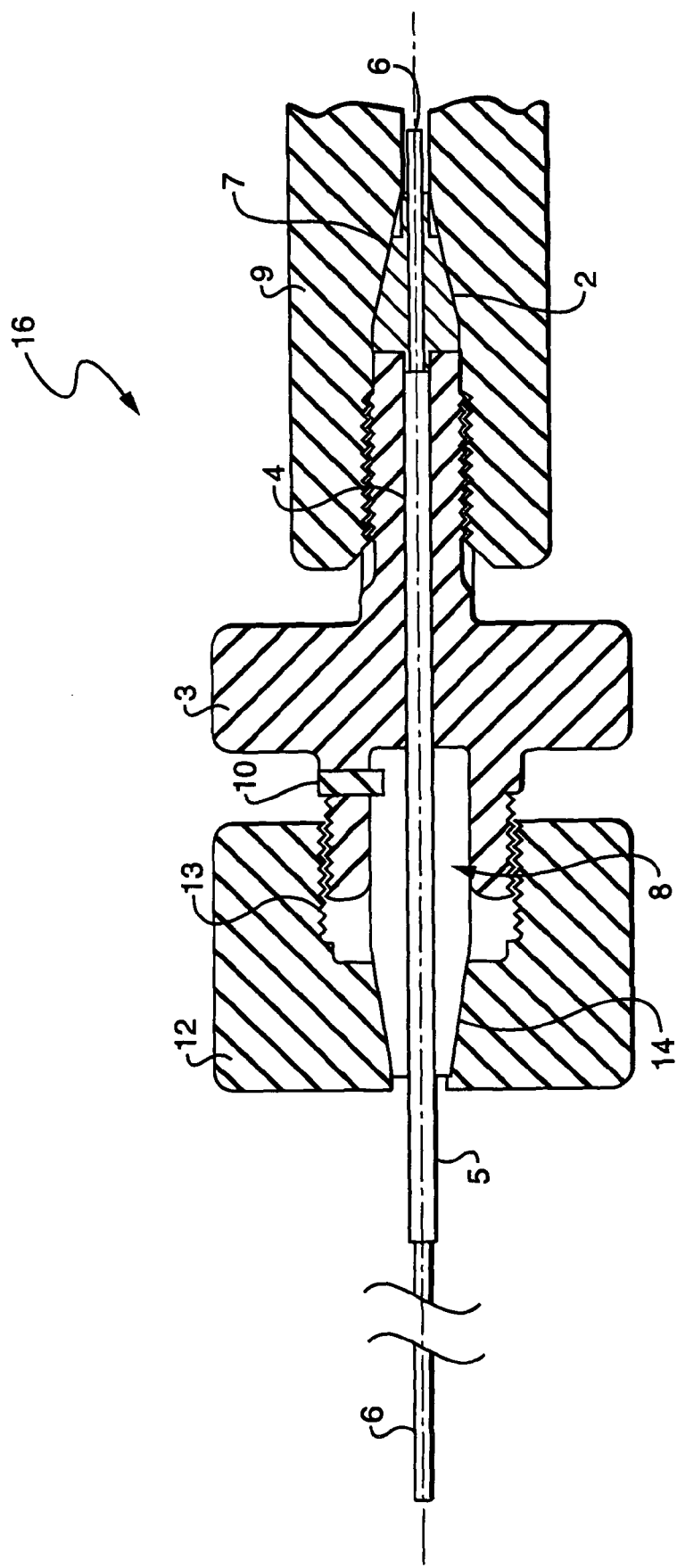
FIG. 1 is a cross sectional view of one embodiment of the invention.

An embodiment of the present invention, a fitting generally designated by the number 16 is depicted in FIG. 1. The fitting is for holding a capillary 6 which uses a forward ferrule 2 and compression screw 3 at a distal end with a single clamping nut 12 that tightens on a clamping collet 8 at a proximal end. The forward ferrule 2 has an axial bore (not shown) to house the capillary 6. An axial bore 4, aligned with the ferrule axial bore but preferably large enough to accommodate the capillary 6 and a sleeve 5, continues through the compression screw 3. In the preferred embodiment, the ferrule 2 is fitted onto the compression screw 3 which is adapted to be hand tightened to a fluidic component 9. The forward ferrule 2 is substantially frusto-conical and is adapted to be received by a complimentary mated receptacle 7 in the fluidic component 9 providing a substantially fluid tight seal when compressed by the tightening of the compression screw 3.

A clamping collet 8 is coupled to the compression screw 3 and may be prevented from rotating by a locating pin 10 or other geometric arrangement such as an asymmetric flange. The collet 8 has a bore aligned with the bore of the ferrule 2 and compression screw 3. The compression screw 3 is adapted to mate to the clamping nut 12 at its proximal end opposite the forward ferrule 2.

By actuating the clamping nut 12, the collet 8 is compressed radially around the capillary. This is accomplished due to the complimentary frusto-conical shapes of the exterior of the collet 8 and the interior of the clamping nut 12. The radial pressure applied to the capillary 6 passing through the collet 8 by the force of the biased nut 12, restrains the capillary 6 from being ejected out of the fitting by fluid pressure.

In the preferred embodiment, the capillary is within a sleeve 5 to help distribute the radial force from the collet 8 evenly over a portion of the capillary and to protect the capillary. As shown in FIG. 1, the clamping nut 12 is joined to the compression screw 3 by any conventional means but preferably by mated threads 13. At the proximal end of the clamping nut 12 the interior threading 13 stops and an integral frusto-conical head 14 is provided to mate with the collet 8. The bias of this head portion 14 actuates the clamping pressure of the collet 8.

When the elements of the fitting are combined, a bore is provided to house and hold the capillary from the distal end of the ferrule 2 to the proximal end of the collet 8.

Figure 2:
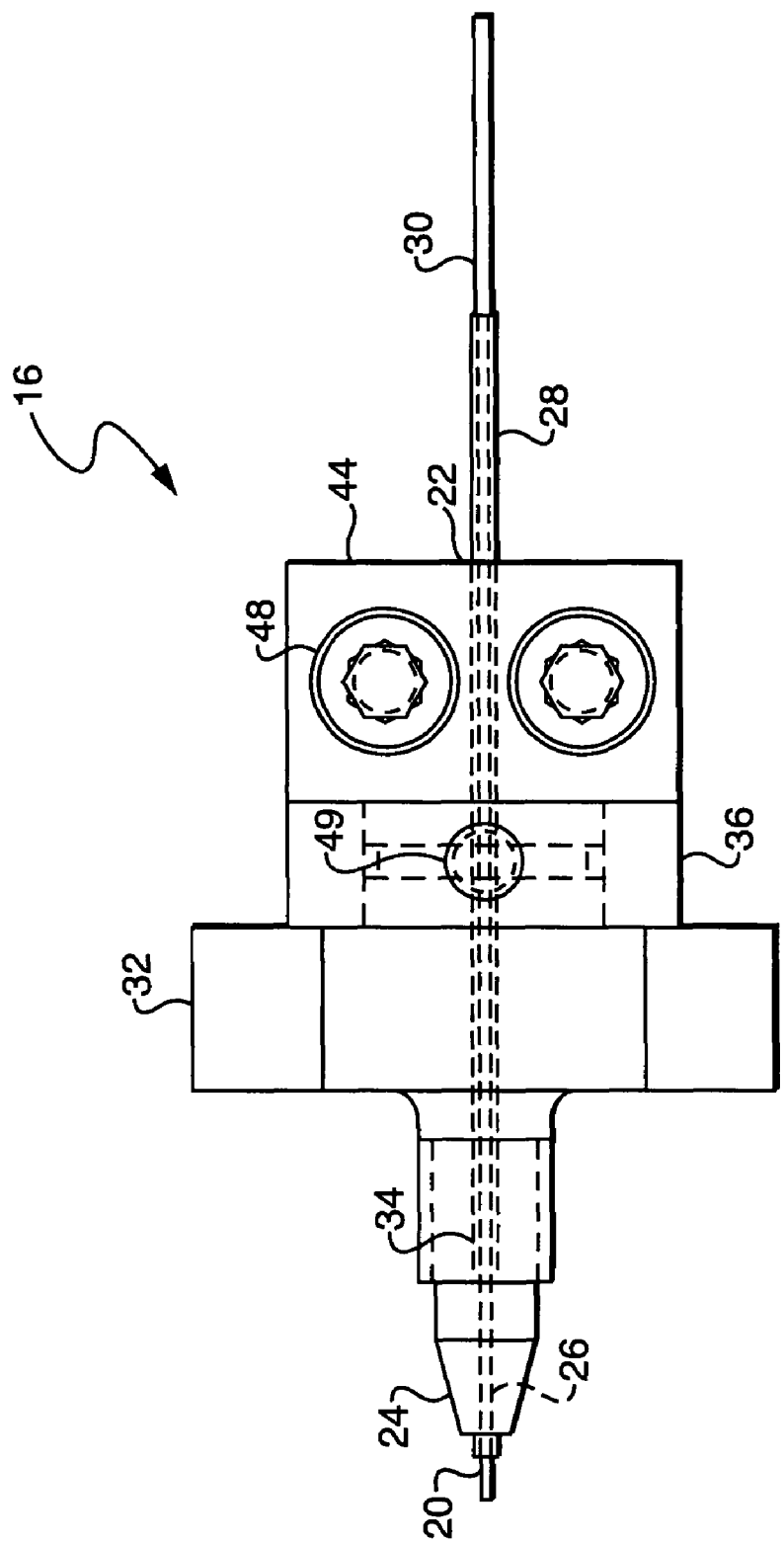
FIG. 2 is an illustration of one embodiment of the invention.

A further embodiment of the interconnection fitting, shown in FIG. 2, has a distal end 20 and a proximal end 22. At the distal end 20 is a forward fluidic sealing ferrule 24. The ferrule 24 has an axial bore 26 for holding a capillary 30. A compression screw 32 is coupled to the forward ferrule 24 forming a high unit pressure fluid seal between ferrule 24 and both capillary 30 and the receptacle installed in a fluidic component (not shown) when the compression screw 32 is tightened into the fluidic component. The compression screw 32 has an axial bore 34 constructed to align with the bore through the forward ferrule 24 and accommodate both the capillary 30 and a capillary sleeve 28. Alternately, the bore 34 through the compression screw may be sized to receive and support just the capillary.

Figure 3:
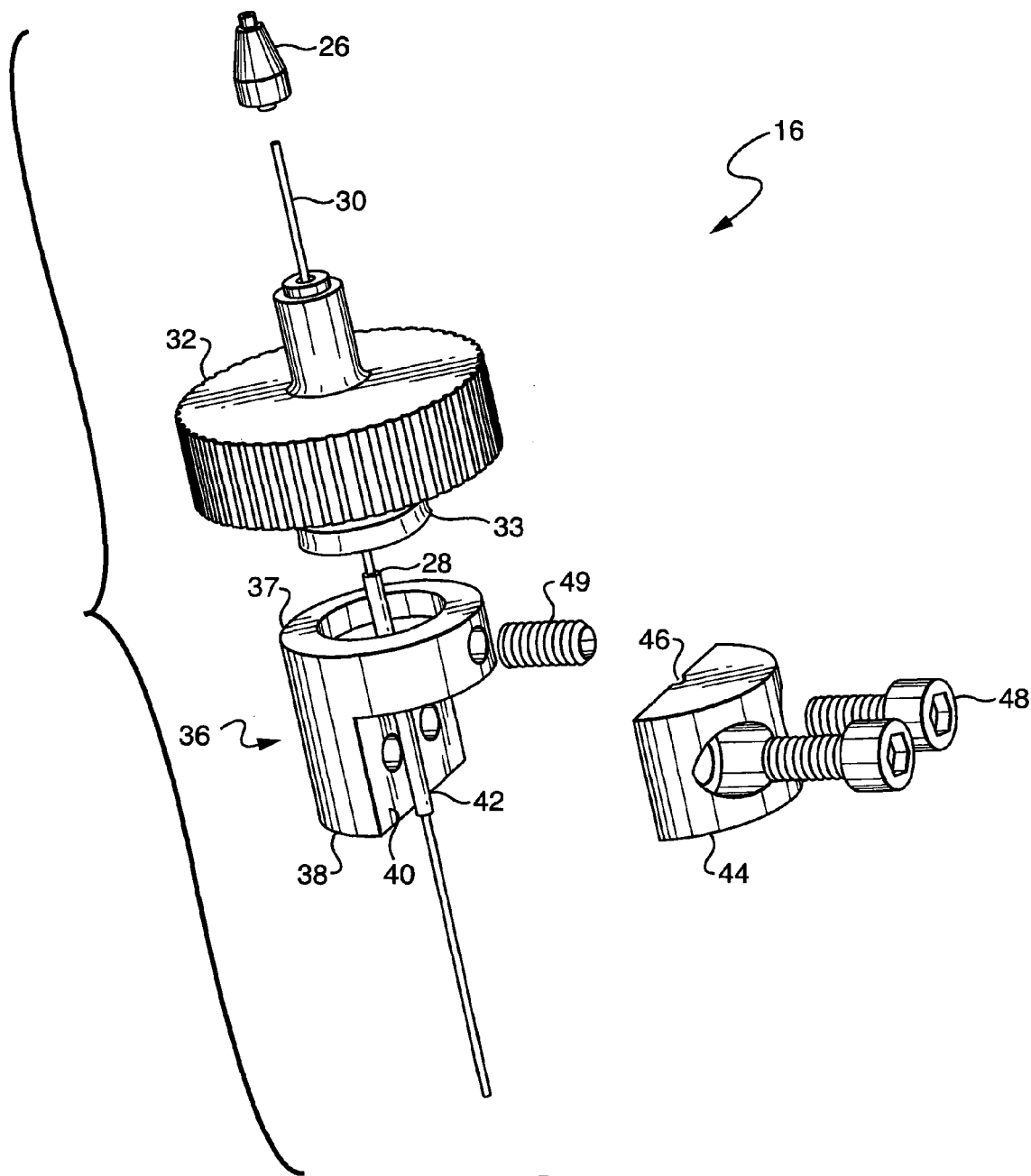
FIG. 3 is an exploded view of the embodiment of FIG. 2.

A clamping collar 36 is coupled to the proximal end of the compression screw 32. Preferably, the clamping collar 36 has a cylindrical 37 and semi-cylindrical portion 38 with a planar side 40 as shown in FIG. 3. The coupling of the clamping collar 36 may be accomplished by having the cylindrical end 37 of this embodiment be an integral part of the compression screw 32. Alternately, the clamping collar may be joined to the compression screw 32 with the aid of a set screw 49 that rests in a groove 33 in the compression screw as in FIG. 3. This set screw 49 acts as a positioning and anti-rotation screw; allowing rotation of the collar 36 around the proximal end of the compression screw 32 when loosened to position the clamping screws 48 for easy access for tightening and preventing the collar 36 from rotating on the compression screw 32 when fully engaged. The planar side 40 of the clamping collar 36 has an axial passage 42. A clamping plate 44 is preferably semi-cylindrical to mate with the clamping collar 36. The plate has an axial passage 46 that corresponds to the passage of the collar 42 such that when the two are engaged, an axial bore is established that aligns with the bore through the forward ferrule 26 and compression screw 32.

The clamping plate 44 is preferably engaged with the collar 36 by two clamping screws 48 placed on either side of the established bore and through the plate 44 and collar 36. By tightening down on the clamping screws 48 a resultant normal clamping pressure is applied to the capillary 30 and sleeve 28 sufficient to prevent the capillary 30 from being forced out of the assembly.

Figure 4:
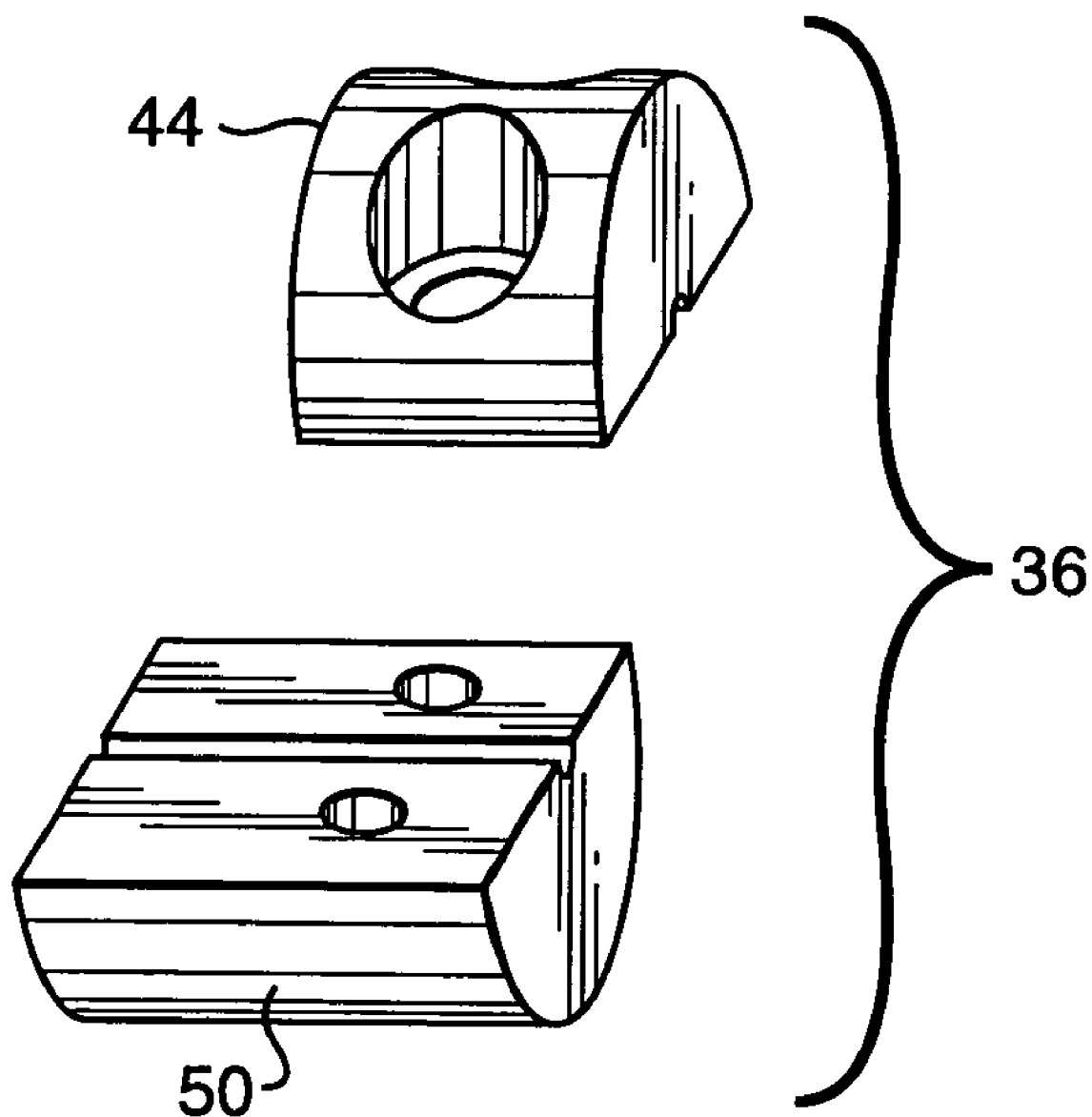
FIG. 4 is an illustration of one embodiment of a clamping device.

The collar 36 may be entirely composed of semi-cylindrical parts as in FIG. 4. The larger part 50 of this embodiment of the collar 36 may be integral to the compression screw 32 or a set screw (not shown) similar to the set screw of the previous embodiment may be utilized to connect this part 50 of the collar 36 to the compression screw 32.

In a further embodiment, the capillary is sleeveless. Here, the bore of the clamping collar 36 may be lined with an appropriate material, such as a polyimide coating, to give the capillary protection and provide a means for distributing the force applied by the clamping device.

Figure 5:
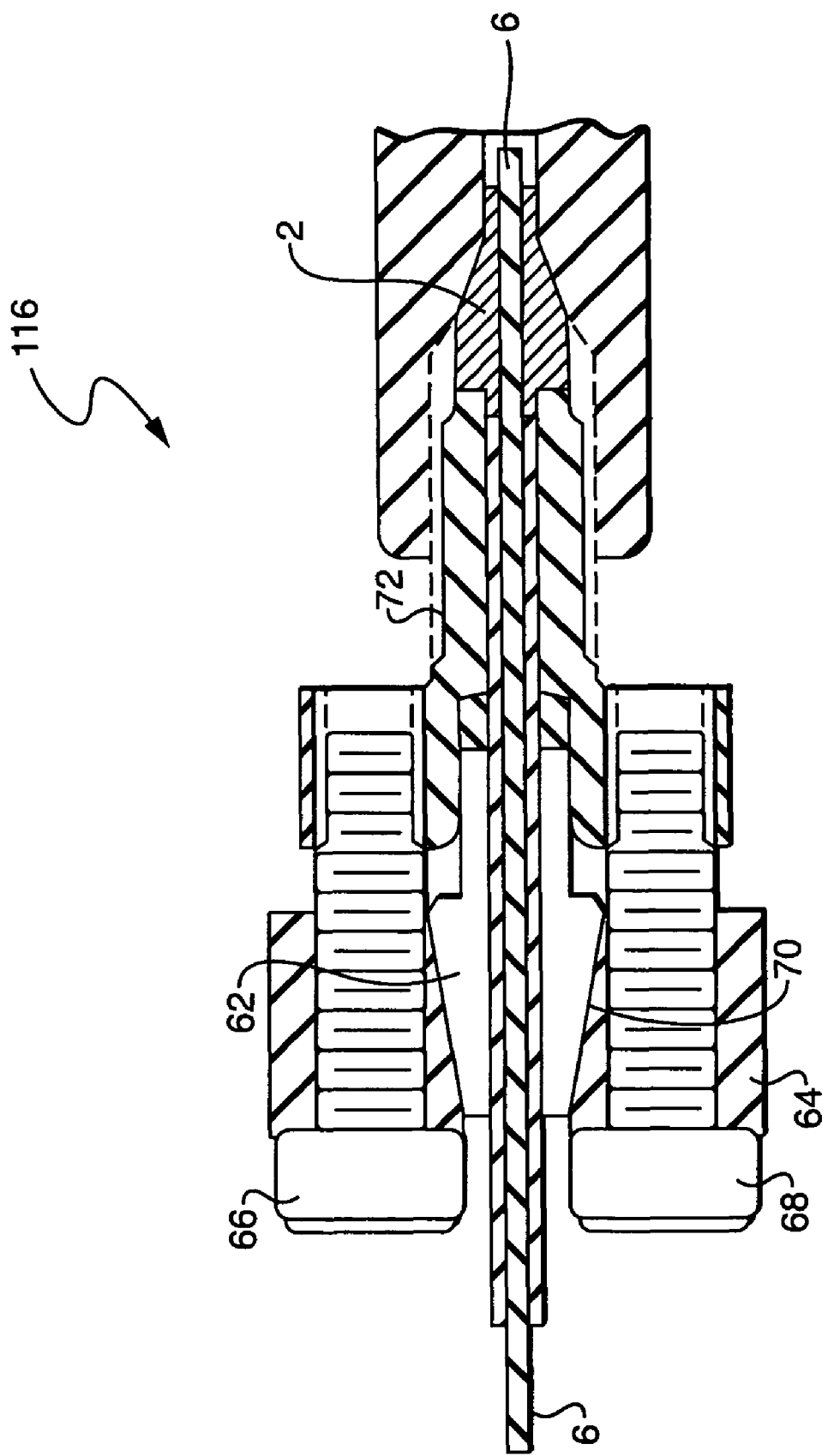
FIG. 5 is a cross sectional view of one embodiment of the invention.

Another embodiment, depicted in FIG. 5, implements the fitting 116 using a similar forward ferrule 2 and clamping collet 62 construction as in FIG. 1. The clamping collet 62 of this embodiment is actuated by a complimentary clamping collar 64. The clamping collar 64 relies on two activating screws 66 and 68 provided on either side of its biased bore 70 that has a complementary shape to the collet 62. The compression screw 72 is adapted to receive the activating screws 66 and 68. As the activating screws 66 and 68 are tightened the biased bore 70 of the clamping collar 64 causes sufficient resultant force normal to the collet 62 to prevent the capillary from ejecting from the fitting.

Fluidic components for which the fitting may be adapted include another capillary, a port associated with a pump, manifold, valve, injector, analytic column, detector flow cell, spray or other device in the fluidic path. The collets and ferrules of the embodiments may be manufactured of a soft metal such as brass or a polymer that is inert to the fluids to be used as is known in the art.

The fitting may be supplied as a kit that can be assembled in the field as needed. Such a kit would include the ferrule, compression screw, and clamping collar of one of the embodiments previously described.

To utilize such a kit, a capillary with at least one free end is passed through, but not tightened into, the clamping collar and compression screw. If the capillary is sleeved, the sleeve is removed from the portion of the capillary extending beyond the compression screw. The ferrule is threaded onto the capillary and butted against the compression screw. The capillary is trimmed to the desired length beyond the ferrule. The capillary, ferrule and compression screw are placed in the fluidic component female receptacle, and the compression screw is screwed into the receptacle until seated, which will assure that the capillary is gripped by the ferrule and that the ferrule is sealingly engaged with the fluidic component. The clamping collar is now connected with the compression screw so that its clamping surfaces will not rotate. Then the clamping collar is tightened onto the capillary (and sleeve if present) with sufficient force to assure that the capillary will not be expelled from the fitting when the interconnect is put under pressure.

Accordingly, it should be readily appreciated that the fitting of the present invention has many practical applications. Additionally, although the preferred embodiment has been illustrated and described, it will be obvious to those skilled in the art that various modifications can be made without departing from the spirit and scope of this invention. Such modifications are to be considered as included in the following claims unless the claims expressly recite differently.

What is claimed:

1. A capillary interconnection fitting comprising:
    a forward fluidic sealing ferrule with an axial bore adapted to receive a capillary and a distal end adapted to connect to a fluidic component;
    a compression screw receiving the proximal end of the ferrule at a distal end having an axial bore aligned with the bore of the ferrule; and
    a clamping device connected to the proximal end of the compression screw and adapted to provide clamping pressure to the capillary; and the clamping device comprises a clamping collet that is activated by a clamping nut having a frusto-conical interior the bias of which is complimentary to the collet and adapted to mate to the distal end of the compression screw.

2. A fitting as in claim 1 further comprising:
    a locating pin that passes through a portion of the compression screw and the collet whereby the collet is held in place relative to the compression screw.

3. A fitting as in claim 1 wherein:
    the clamping nut mates to the compression screw by complimentary threaded means.

4. The fitting as in claim 1 further comprising a capillary sleeve adapted to be disposed about the length of the capillary, interior to the clamping device and the compression screw.

5. A fitting as in claim 4 wherein:
    the diameter of the bore through the forward ferrule narrows at its distal end preventing the capillary sleeve from passing fully through the ferrule and for allowing only a capillary to pass fully through the ferrule.

6. A fitting as in claim 4 wherein:
    the clamping device comprises a clamping collet that is activated by a clamping collar with a biased bore adapted to activate the collet.

* * * * *